(12) United States Patent
Ishida et al.

(10) Patent No.: US 7,947,802 B2
(45) Date of Patent: May 24, 2011

(54) BENZOXAZINE MONOMERS, POLYMERS AND COMPOSITIONS

(75) Inventors: Hatsuo Ishida, Shaker Heights, OH (US); Pedro Velez-Herrera, Washington, DC (US)

(73) Assignee: Case Western Reserve University, Cleveland, OH (US)

( * ) Notice: Subject to any disclaimer, the term of this patent is extended or adjusted under 35 U.S.C. 154(b) by 646 days.

(21) Appl. No.: 11/899,438

(22) Filed: Sep. 6, 2007

(65) Prior Publication Data

US 2009/0069533 A1    Mar. 12, 2009

(51) Int. Cl.
- C08G 73/06 (2006.01)
- C08G 63/00 (2006.01)
- C07D 265/06 (2006.01)
- C07D 265/14 (2006.01)
- C07D 413/04 (2006.01)
- C07D 498/04 (2006.01)

(52) U.S. Cl. ........ 528/423; 528/424; 528/425; 528/360; 528/361; 544/73; 544/63; 544/69; 544/74; 544/88; 544/90; 544/96; 544/105

(58) Field of Classification Search ............ 544/73, 544/63, 69, 74, 90, 105, 88, 96; 528/423, 528/424, 425, 360, 361
See application file for complete search history.

(56) References Cited

U.S. PATENT DOCUMENTS

| | | | |
|---|---|---|---|
| 5,152,939 A | 10/1992 | Ishida | |
| 5,266,695 A | 11/1993 | Ishida | |
| 5,294,461 A | 3/1994 | Ishida | |
| 5,543,516 A | 8/1996 | Ishida | |
| 5,900,447 A | 5/1999 | Ishida | |
| 5,973,144 A | 10/1999 | Ishida | |
| 6,160,042 A | 12/2000 | Ishida | |
| 6,160,079 A | 12/2000 | Ishida et al. | |
| 6,207,786 B1 | 3/2001 | Ishida et al. | |
| 6,225,440 B1 | 5/2001 | Ishida | |
| 6,323,270 B1 | 11/2001 | Ishida | |

OTHER PUBLICATIONS

Marrero et al; Atom—antibacterial activity; Mar. 2005, 13(8), 2881-2899; Elsevier Ltd; Chem Abstract 143: 307.*
Saito et al; Benzoxazines—elastic modulus; 2002; Mitsubishi rayon Co., Ltd., Japan; Chem Abstract 137: 311666.*
Hemwall; Improving—clay containing soils; 1964; Dow Chemical Co., Chem Abstract 61: 21313.*
Hemwall; Improving—clay containing soils; 1964; Dow Chemical Co., Chem Abstract 60 : 81551.*

* cited by examiner

*Primary Examiner* — Duc Truong
(74) *Attorney, Agent, or Firm* — Hudak, Shunk & Farine Co. LPA

(57) ABSTRACT

Benzoxazine monomers comprising at least one pendant group are described. (Co)Polymers comprising at least one benzoxazine monomer having at least one pendant group are also described. In a preferred embodiment, the pendant group is located in a side chain of the benzoxazine monomer or polymer. Methods for preparing the benzoxazine monomers and polymers are described. Compositions comprising the benzoxazine monomers and polymers have numerous uses including optical materials, and in electronic materials as electrically insulating materials, and as fireproof materials.

20 Claims, 1 Drawing Sheet

DSC thermograph (S2-4)

FIG. 1  DSC thermograph (S2-4)
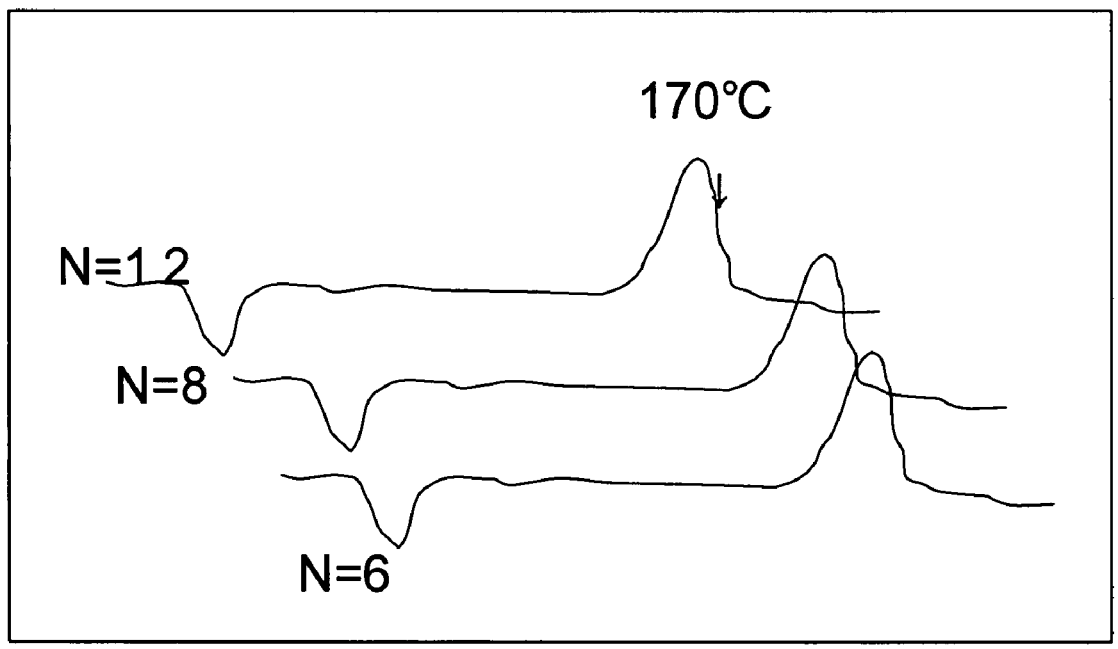
FIG. 2  FTIR spectra (S2-4)
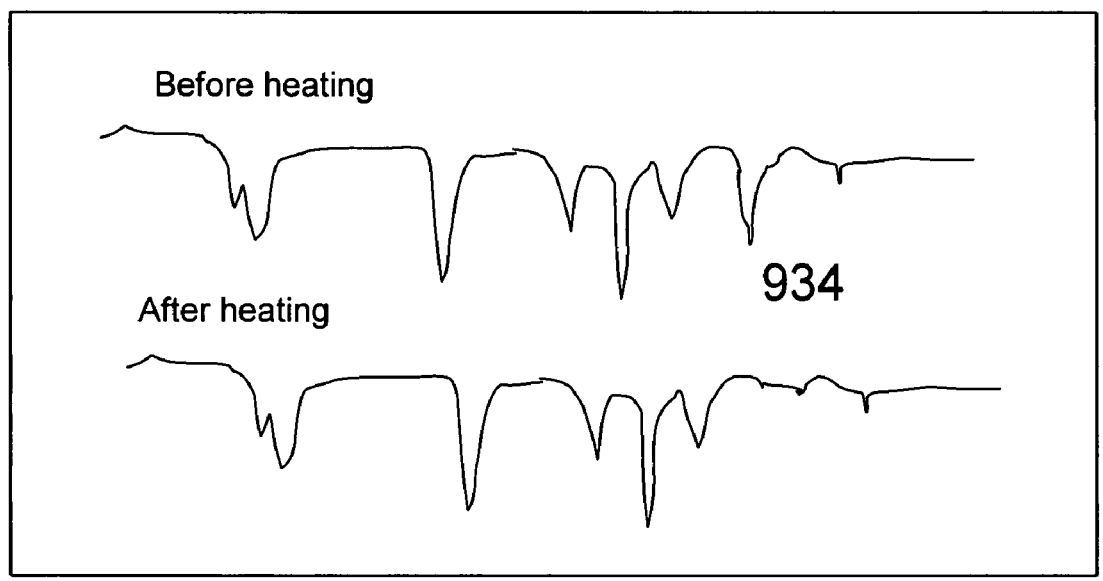

BENZOXAZINE MONOMERS, POLYMERS AND COMPOSITIONS

FIELD OF THE INVENTION

The present invention relates to benzoxazine, naphthoxazine and anthranoxazine monomers and polymers comprising at least one pendant or branch group. In one embodiment, at least one pendant group forms a side chain of the benzoxazine polymers. Methods for preparing the benzoxazine monomers and polymers are described below. Compositions comprising the benzoxazine monomers and polymers have numerous uses including optical materials, and in electronic materials as electrically insulating materials, and as fireproof materials.

BACKGROUND OF THE INVENTION

Benzoxazine compounds have numerous uses and compete with phenol, epoxy, and other thermoset or thermoplastic resins in various applications. Benzoxazine compounds can be used in applications where insulating materials are needed or where fireproof materials are desired.

Small molecular weight benzoxazine chemistry has been around for more than 50 years since the first work was reported in 1944. However, the use of benzoxazines as precursors for a class of thermosetting resins with useful dielectric properties and thermal properties had been recognized only recently. Polybenzoxazines show a number of attractive properties, including high glass transition temperature (Tg), high thermal stability, excellent dielectric properties, and wide molecular design flexibility.

Various disclosures regarding benzoxazine monomers, polymers and compositions are set forth in the following references: U.S. Pat. Nos. 5,152,939; 5,266,695; 5,543,516; 5,900,447; 5,973,144; 6,160,079; 6,207,786; 6,225,440 and 6,323,270, herein fully incorporated by reference.

SUMMARY OF THE INVENTION

Pendant group-containing benzoxazine-type monomers, such as benzoxazine, naphthoxazine and anthranoxazine monomers and methods for their preparation are described in the present invention. Polymers and compositions derived from the pendant group-containing benzoxazine monomers are also disclosed along with routes for preparation thereof. Many different types of pendant groups of various lengths and structures can be used to provide useful properties.

Both mono- and poly-functional benzoxazine-type monomers are utilized in the present invention. The pendant groups are connected to the benzoxazines through one or more of the phenolic- or amine-derived portion of the benzoxazine monomer or polymer.

Accordingly, it is one object of the present invention to provide mono- and poly-functional benzoxazine monomers and/or polymers and compositions including the same wherein the benzoxazines include a defined pendant group connected to one or more of the phenolic- or amine-derived portion of the benzoxazine.

A further object of the present invention is to provide benzoxazine monomers and polymers having a pendant group comprising at least one relatively rigid segment, and more preferably a rigid segment and an additional substituent.

It is a further object of the present invention to provide benzoxazine monomers and polymers with pendant groups that include a rigid segment, preferably one or more hydrocarbon rings optionally containing heteroatoms and an additional substituent comprising one or more of an alkoxy group and a carbonyl group.

As utilized within the present invention, the terms benzoxazine or benzoxazine-type refer to compounds containing at least a characteristic benzoxazine structure and, therefore include, for example, benzoxazine-, naphthoxazine- and anthranoxazine-based compounds.

In one aspect of the invention, a benzoxazine group-containing monomer having a pendant group is disclosed, comprising:

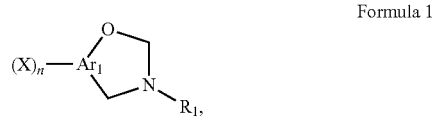

Formula 1

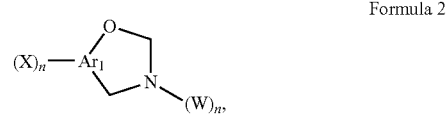

Formula 2

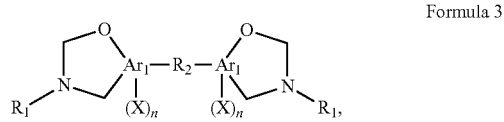

Formula 3

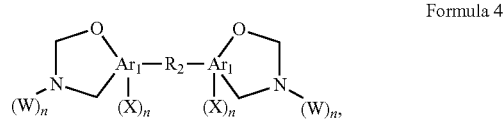

Formula 4

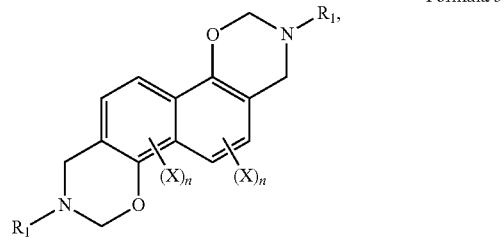

Formula 5

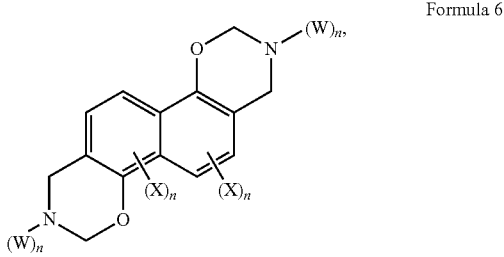

Formula 6

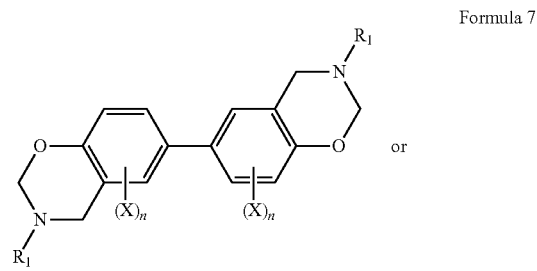

Formula 7 or

-continued

Formula 8

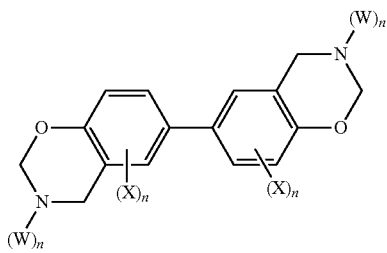

wherein each n, independently, is an integer from 0 to 2, with the proviso that at least one n of each formula is 1 or 2;

wherein each $Ar_1$, independently is one or more optionally substituted aromatic rings having from 6 to 18 carbon atoms, wherein each $R_1$, independently, is a linear or branched, optionally substituted, alkyl group, for example having from 1 to about 18 carbon atoms, a mono- or polyfluorinated alkyl having from 1 to about 9 carbon atoms, an aromatic having from 6 to about 18 carbon atoms, or an alkyl substituted aromatic or aromatic substituted alkyl of 7 to about 40 carbon atoms;

wherein $R_2$ comprises:

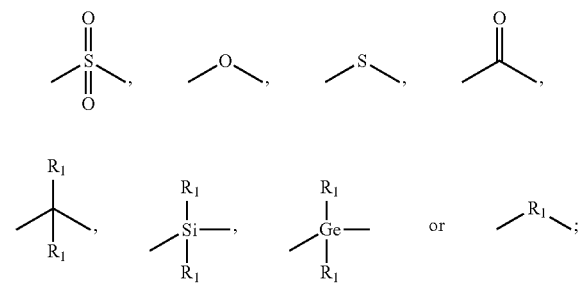

wherein X is —Z—Y-Sp-Z—Y—SP—Z—Y-Sp; wherein one or more Z, Y, or Sp are optionally absent, with the proviso that at least one Z is present and when one or more Z, Y or Sp are absent, the present adjacent components are directly connected;

wherein each Z, independently, is selected from one of the following rings:

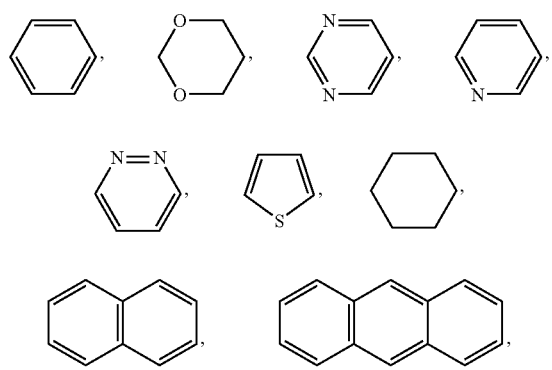

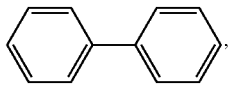

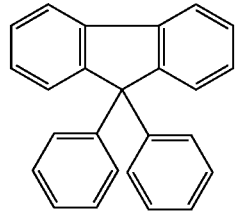

wherein any of the Z rings, independently, is optionally substituted with one or more of the following substituents in at least one of the available substitution positions: F, Cl, Br, $CH_3$, CN, OR, R and NCS where R is a branched or straight chain alkyl having from 1 to about 5 carbon atoms;

wherein each Y, independently, is selected from COO, OCO, $CH_2$, $CHCH_2CH_2$, $CH_2O$, $OCH_2$, —$C(CH_3)_2$—, O, S, N, CH=N, $C(CH_3)$=N, $C(CH_3)$=CH, $C(CH_3)$=$C(CH_3)$, CH=CH or C≡C;

wherein each spacer group Sp, independently, is optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, an alkoxy having from 1 to about 20 carbon atoms, an alkoxycarbonyl having from 1 to about 20 carbon atoms, an alkylcarbonyl having from 1 to about 20 carbon atoms, or an alkylcarbonyloxy having from 1 to about 20 carbon atoms, or a corresponding intermediate chain group with the proviso that when $Ar_1$ is benzene and Z is a hydrocarbon aromatic containing one or more aromatic rings, at least one or more of Y and Sp are present and include one or more heteroatoms;

wherein each W, independently, is —Z—Y-$Sp_w$-Z—Y—$SP_w$-Z—Y-$Sp_w$; wherein one or more Z, Y, or $Sp_w$ are optionally absent with the proviso that at least one Z is present, and when one or more Z, Y, or $Sp_w$ are absent, the present adjacent components are directly connected; and wherein each $Sp_w$, independently, is optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, alkoxy having from 5 to about 20 carbon atoms, alkoxycarbonyl having from 1 to about 20 carbon atoms, alkylcarbonyl having from 1 to about 20 carbon atoms, or alkylcarbonyloxy having from 1 to about 20 carbon atoms, or a corresponding intermediate chain group.

In another aspect of the invention, a method for forming a benzoxazine group-containing monomer is disclosed, comprising the steps of providing a phenol compound, an aldehyde, and a primary amine, wherein at least the primary amine or phenol compound includes at least one pendant group; and forming a pendant group-containing benzoxazine monomer having the following formula:

Formula 1

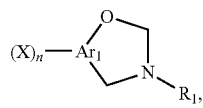

-continued

Formula 2

(X)ₙ—Ar₁—[oxazolidine ring]—(W)ₙ,

Formula 3

R₁—[oxazolidine]—Ar₁—R₂—Ar₁—[oxazolidine]—R₁
         (X)ₙ              (X)ₙ

Formula 4

(W)ₙ—[oxazolidine]—Ar₁—R₂—Ar₁—[oxazolidine]—(W)ₙ,
         (X)ₙ              (X)ₙ

Formula 5

[fused tricyclic oxazine structure with R₁, (X)ₙ]

Formula 6

[fused tricyclic oxazine structure with (W)ₙ, (X)ₙ]

Formula 7

[biphenyl bis-oxazine structure with R₁, (X)ₙ]
or

Formula 8

[biphenyl bis-oxazine structure with (W)ₙ, (X)ₙ]

wherein each n, independently, is an integer from 0 to 2, with the proviso that at least one n of each formula is 1 or 2;

wherein each Ar₁, independently is one or more optionally substituted aromatic rings having from 6 to 18 carbon atoms, wherein each R₁, independently, is a linear or branched, optionally substituted, alkyl group, for example having from 1 to about 18 carbon atoms, a mono- or polyfluorinated alkyl having from 1 to about 9 carbon atoms, an aromatic having from 6 to about 18 carbon atoms, or an alkyl substituted aromatic or aromatic substituted alkyl of 7 to about 40 carbon atoms;

wherein R₂ comprises:

[sulfonyl, ether, thioether, carbonyl groups shown]

[tert-butyl, silyl, germyl groups with R₁, or CHR₁ group];

wherein X is —Z—Y-Sp-Z—Y—SP—Z—Y-Sp; wherein one or more Z, Y, or Sp are optionally absent, with the proviso that at least one Z is present and when one or more Z, Y or Sp are absent, the present adjacent components are directly connected;

wherein each Z, independently, is selected from one of the following rings:

[benzene, dioxane, pyrazine, pyridine, pyridazine, thiophene, cyclohexane, naphthalene, anthracene, biphenyl, or fluorene with two phenyl substituents]

wherein any of the Z rings, independently, is optionally substituted with one or more of the following substituents in at least one of the available substitution positions: F, Cl, Br, CH₃, CN, OR, R and NCS where R is a branched or straight chain alkyl having from 1 to about 5 carbon atoms;

wherein each Y, independently, is selected from COO, OCO, CH₂, CHCH₂CH₂, CH₂O, OCH₂, —C(CH₃)₂—, O, S, N, CH═N, C(CH₃)═N, C(CH₃)═CH, C(CH₃)═C(CH₃), CH═CH or C≡C;

wherein each spacer group Sp, independently, is optionally substituted, saturated or unsaturated, straight chain or branched chain alkyl or alkylene group having from 1 to about 80 carbon atoms, with one or more of the non-adjacent alkyl CH₂ groups being optionally replaced by one or more heteroatoms, an alkoxy having from 1 to about 20 carbon atoms, an alkoxycarbonyl having from 1 to about 20 carbon atoms, an alkylcarbonyl having from 1 to about 20 carbon atoms, or an alkylcarbonyloxy having from 1 to about 20 carbon atoms, or a corresponding intermediate chain group with the proviso that when Ar₁ is benzene and Z is a hydrocarbon aromatic containing one or more aromatic rings, at least one or more of Y and Sp are present and include one or more heteroatoms;

wherein each W, independently, is —Z—Y-Sp$_w$-Z—Y—SP$_w$-Z—Y-Sp$_w$; wherein one or more Z, Y, or Sp$_w$ are optionally absent with the proviso that at least one Z is present, and when one or more Z, Y, or Sp$_w$ are absent, the present adjacent components are directly connected; and wherein each Sp$_w$, independently, is optionally substituted, saturated or unsaturated, straight chain or branched chain alkyl or alkylene group having from 1 to about 80 carbon atoms, with one or more of the non-adjacent alkyl CH$_2$ groups being optionally replaced by one or more heteroatoms, alkoxy having from 5 to about 20 carbon atoms, alkoxycarbonyl having from 1 to about 20 carbon atoms, alkylcarbonyl having from 1 to about 20 carbon atoms, or alkylcarbonyloxy having from 1 to about 20 carbon atoms, or a corresponding intermediate chain group.

BRIEF DESCRIPTION OF THE DRAWINGS

The invention will be better understood and other features and advantages will become apparent by reading the detailed description of the invention, taken together with the drawings, wherein:

FIG. 1 is a DSC thermogram of pendant group-containing benzoxazine monomers of formula S2-4 having a 6, 8 or 12 methylene unit spacer group.

FIG. 2 is a FT-IR spectra before and after heating of pendant group-containing benzoxazine monomers of formula S2-4 having a 12 methylene unit spacer group.

DETAILED DESCRIPTION OF THE INVENTION

Benzoxazine Monomers Comprising a Pendant Group

The present invention discloses pendant group-containing benzoxazine-type monomers having the following formulae:

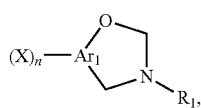

Formula 1

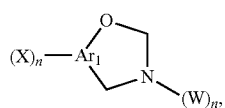

Formula 2

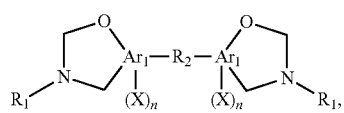

Formula 3

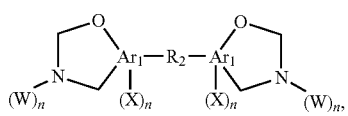

Formula 4

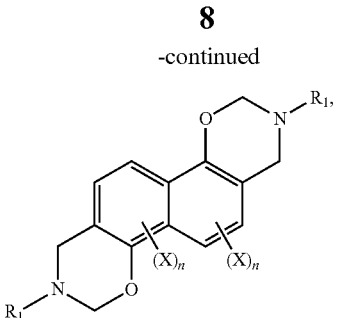

Formula 5

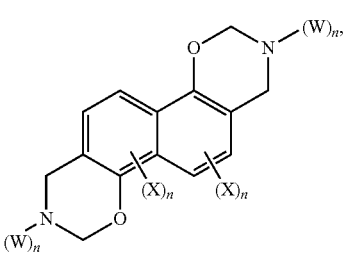

Formula 6

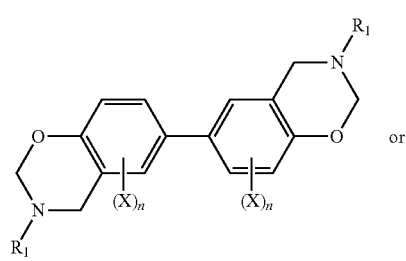

Formula 7

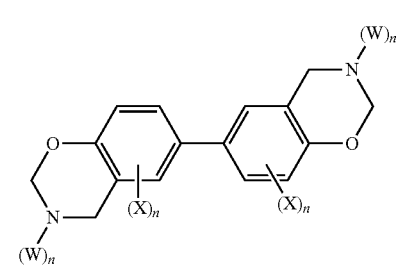

Formula 8 wherein each n, independently, is an integer from 0 to 2, with the proviso that at least one n of each formula is 1 or 2;

wherein each Ar$_1$, independently, is derived from one or more aromatic rings having from 6 to 18 carbon atoms, such as a benzene ring, naphthalene rings, or anthracene rings, wherein Ar$_1$ is optionally substituted, with examples of suitable substituents including, but not limited to, one or more of a linear or branched alkyl group, for example having from 1 to about 18 carbon atoms, and preferably from 1 to about 12 carbon atoms;

wherein each R$_1$, independently, is a linear or branched, optionally substituted, alkyl group, for example having from 1 to about 18 carbon atoms, and preferably from 1 to about 12 carbon atoms, a mono- or polyfluorinated alkyl having from 1 to about 9 carbon atoms such as CF$_3$, C$_2$F$_5$, C$_3$F$_7$, an aromatic having from 6 to about 18 carbon atoms, or an alkyl substituted aromatic or aromatic substituted alkyl of 7 to about 40 carbon atoms;

wherein R$_2$ comprises:

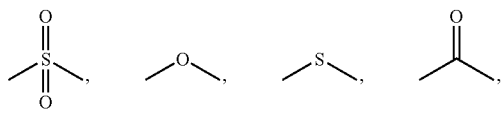

-continued

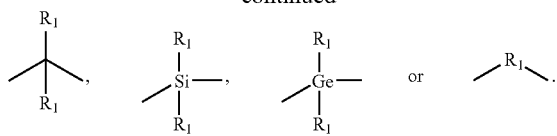

wherein X is a pendant group comprising at least one relatively rigid segment and is further defined as —Z—Y-Sp-Z—Y—SP—Z—Y-Sp;

wherein one or more Z, Y, or Sp may be absent, with the proviso that at least one Z is present, and it is to be understood that when a Z, Y or Sp is absent, the present adjacent components are directly connected. For example, X can be —Z-Sp-Z—Y; and wherein each Z, independently, is selected from one of the following rings:

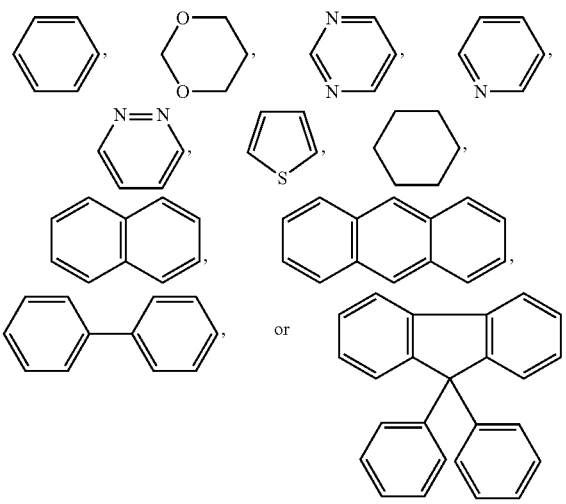

wherein, any of the Z rings, independently, can be substituted with one or more of the following substituents in at least one of the available substitution positions: F, Cl, Br, $CH_3$, CN, OR, R and NCS where R is a branched or straight chain alkyl having from 1 to about 5 carbon atoms;

wherein each Y, independently, is selected from COO, OCO, $CH_2$, $CHCH_2CH_2$, $CH_2O$, $OCH_2$, —$C(CH_3)_2$—, O, S, N, CH=N, $C(CH_3)$=N, $C(CH_3)$=CH, $C(CH_3)$=$C(CH_3)$, CH=CH or C≡C;

wherein each spacer group Sp, independently, includes, but is not limited to, optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, an alkoxy having from 1 to about 20 carbon atoms, preferably an alkoxy having from 5 to about 20 carbon atoms, an alkoxycarbonyl having from 1 to about 20 carbon atoms, an alkylcarbonyl having from 1 to about 20 carbon atoms, or an alkylcarbonyloxy having from 1 to about 20 carbon atoms, or a corresponding intermediate chain group, with the proviso that when $Ar_1$ is benzene and Z is a hydrocarbon aromatic containing one or more aromatic rings, at least one or more of Y and Sp are present and include one or more heteroatoms, preferably at least one oxygen atom;

wherein each W, independently, is —Z—Y-$Sp_w$-Z—Y—$SP_w$-Z—Y-$Sp_w$;

wherein Z and Y are defined hereinabove;

wherein each W spacer group $Sp_w$, independently, includes, but is not limited to, optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, alkoxy having from 5 to about 20 carbon atoms, alkoxycarbonyl having from 1 to about 20 carbon atoms, alkylcarbonyl having from 1 to about 20 carbon atoms, or alkylcarbonyloxy having from 1 to about 20 carbon atoms, or a corresponding intermediate chain group. It is to be understood that when one or more of Z, Y or $Sp_w$ are absent, the present adjacent components are directly connected. For example, X can be —Z-$Sp_w$-Z—Y.

In preferred embodiments, the pendant group X comprises at least one relatively rigid group, Z, such as an aromatic ring, and preferably, at least one spacer group, Sp, preferably one or more of an alkoxy group, carboxyl group, or a combination thereof. In some embodiments, the relatively rigid group is directly connected to the benzoxazine portion of the compound. In other embodiments, the spacer group or another group is directly connected to the benzoxazine portion of the compound and the relatively rigid group is located in an intermediate or terminal position of the pendant-containing compound. Due to the adaptability of arrangement of the components of the pendant-containing group, numerous different structures having beneficial properties can be formed.

Each spacer group, Sp, independently includes, but is not limited to, optionally substituted saturated or unsaturated, straight chain or branched chain alkyl or alkylene group having from 1 to about 80 carbon atoms, with one or more of the non-adjacent alkyl $CH_2$ groups being optionally replaced by one or more heteroatoms. The spacer groups can include alkyl having from 1 to about 20 carbon atoms and preferably from 4 to about 20 carbon atoms, alkoxy having from 1 to about 20 carbon atoms and preferably from 5 to about 20 carbon atoms, alkoxycarbonyl having from 1 to about 20 carbon atoms, alkylcarbonyl having from 1 to about 20 carbon atoms, or alkylcarbonyloxy groups having from 1 to about 20 carbon atoms, for example, methyl, ethyl, propyl, butyl, pentyl, hexyl, heptyl, octyl, nonyl, decyl, undecyl, dodecyl, methoxy, ethoxy, n-propoxy, i-propoxy, butoxy, pentyloxy, hexyloxy, heptyloxy, octyloxy, nonyloxy, decyloxy, undecyloxy, dodecyloxy, methoxycarbonyl, ethoxycarbonyl, propoxycarbonyl, butoxycarbonyl, pentyloxycarbonyl, hexyloxycarbonyl, octyloxy-carbonyl, nonyloxycarbonyl, decyloxycarbonyl, undecyloxycarbonyl, dodecyloxy-carbonyl, methylcarbonyl, ethylcarbonyl, propylcarbonyl, butylcarbonyl, pentylcarbonyl, hexylcarbonyl, octylcarbonyl, nonylcarbonyl, decylcarbonyl, undecylcarbonyl, dodecylcarbonyl, methylcarbonyloxy, ethylcarbonyloxy, propylcarbonyloxy, butylcarbonyloxy, pentylcarbonyloxy, hexylcarbonyloxy, octylcarbonyloxy, nonylcarbonyloxy, decylcarbonyloxy, undecylcarbonyloxy, or dodecylcarbonyloxy, or corresponding inter-mediate chain groups, e.g., —(SP)—, and the like.

The optionally substituted alkyl groups having from 1 to about 80 carbon atoms may be substituted by alkyl, aryl and cycloalkyl, as well as amino, cyano, epoxy, halogen, hydroxyl, nitro, oxo, etc. Possible heteroatoms, which may replace carbon atoms, include nitrogen, oxygen and sulfur. In the case of nitrogen, further substitution is possible with groups such as alkyl, aryl and cycloalkyl. The optionally substituted aromatic or non-aromatic carboxylic or heterocyclic ring systems may be similarly substituted. The spacer group, Sp, can be directly or indirectly connected to the benzoxazine portion of the compound.

Specific examples of pendant groups, X and W, independently, include, but are not limited to:
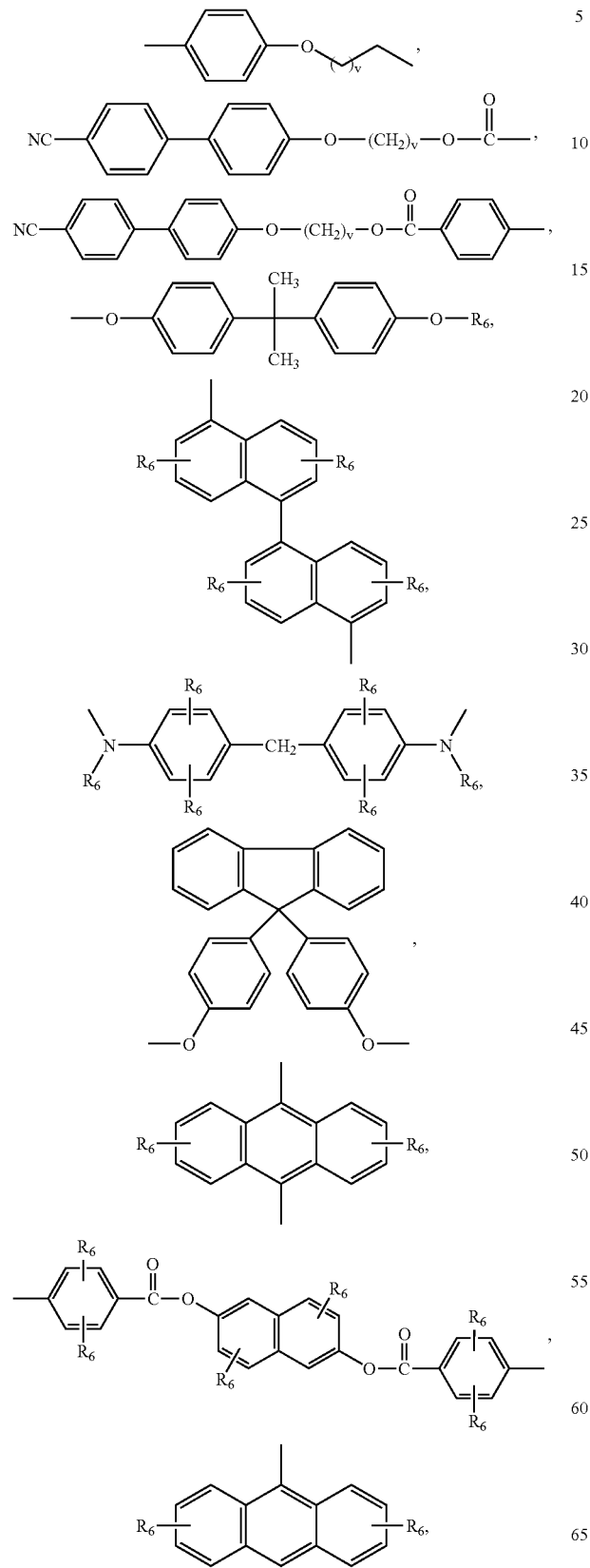
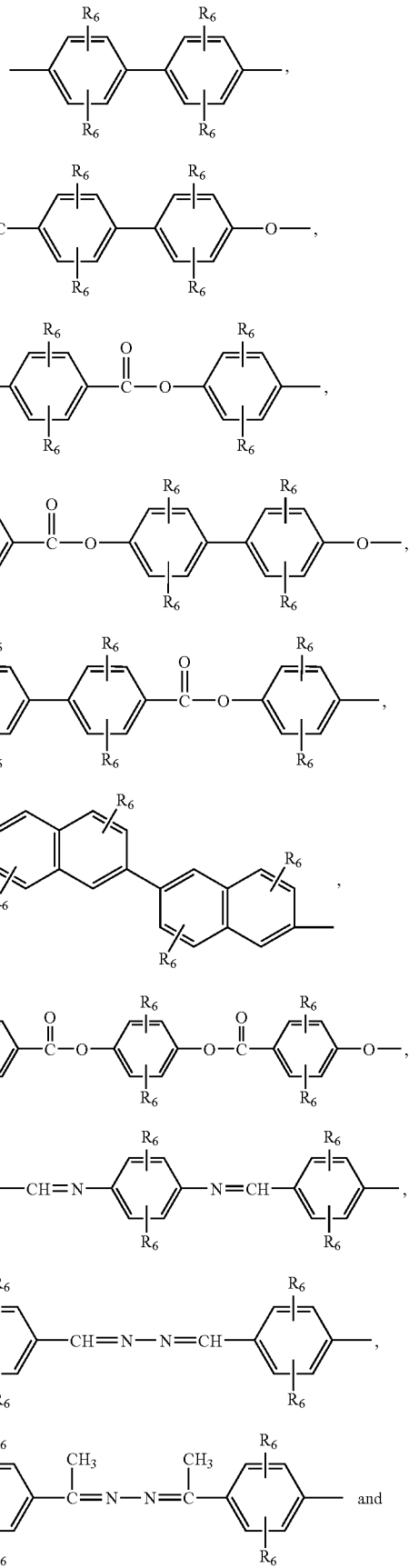

-continued

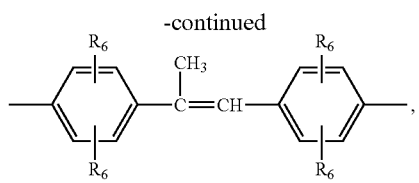

wherein each $R_6$, independently, is hydrogen, an aliphatic group having from 1 to about 12 carbon atoms, or a halogen atom, and wherein v is 1 to about 20.

For example, in one embodiment as described hereinbelow, the pendant group containing benzoxazine monomer has the following formula:

Formula 9

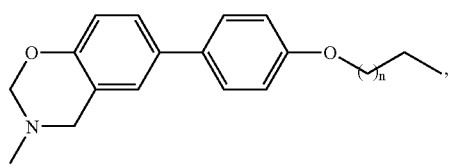

wherein $Ar_1$ is benzene, X is —Z-Sp with Z being $C_6H_4$ and Sp being an alkoxy group, wherein n is 8, 10 or 12 for example. In further examples, as described hereinbelow, the benzoxazine monomers have the formulae:

Formula 10

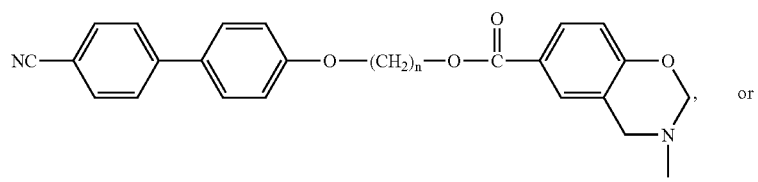

or

Formula 11

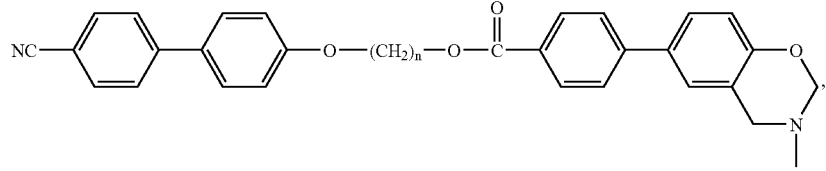

wherein in Formula 10, $Ar_1$ is benzene, X is —Y-Sp-Z—Z with Y being COO, Sp being $(CH_2)_n$—O—, the first Z being $C_6H_4$ and the terminal Z being $C_6H_4$—CN; and wherein in Formula 11, $Ar_1$ is benzene, X is —Z-Y-Sp-Z—Z, with the first Z being $C_6H_4$, Y being COO, Sp being $(CH_2)_n$—O—, the second Z being $C_6H_4$, and the third, terminal Z being $C_6H_4$—CN.

Benzoxazine Monomer Formation

The pendant group-containing benzoxazine monomers are synthesized from the reaction of three main compounds; namely (1) a phenol, optionally having a pendant-containing group, X, (2) an aldehyde or aldehyde derivative, and (3) primary amine, optionally having a pendant-containing group, W, with the proviso that at least one of the phenol or amine components include a pendant group.

The desired pendant groups can be added to the phenol or amine components utilizing any of a number of different procedures, such as described hereinbelow.

For example, in one embodiment of the present invention, a compound including a portion of a pendant group desired to be included in the benzoxazine monomer or polymer is reacted with a phenol to produce a pendant group-containing phenol. In one embodiment, a biphenol or polyphenol is reacted with a halogenated hydrocarbon, such as bromodecane or the like, having from 1 to about 20, and preferably from about 4 to about 20 carbon atoms to form a pendant group-containing phenol also comprising a rigid group and an alkoxy group. The biphenol and halogenated hydrocarbon are added to a reaction vessel, with the halogenated hydrocarbon preferably present in a slightly molar excess. A solvent such as ethanol can also be utilized with the reaction mixture, which is placed under an inert atmosphere, such as nitrogen. A base such as potassium hydroxide is present in the reaction mixture. An effective amount of a catalyst such as potassium iodide in ethanol and water, (90/10) for example, is added, preferably drop-wise over a period of time, such as about 5 hours to the reaction vessel with stirring. The reaction mixture is subsequently stirred at the reflux temperature, which can vary depending on the solvent used, for a suitable period of time to complete the reaction, preferably about 24 hours. The solvent is subsequently evaporated and the reaction mixture concentrated. The reaction product can be dissolved with a solvent, such as ethyl acetate, washed with deionized water, and subsequently dried with sodium sulfate. The evaporated reaction product, a pendant group-containing phenol can be utilized in a subsequent reaction step to prepare the pendant group-containing benzoxazine monomer, and (co)polymers therefrom.

In a further embodiment, a compound including a portion of a pendant group desired to be included in the benzoxazine monomer or polymer and having at least one hydroxyl group is reacted, for example, with a dihalogenated hydrocarbon such as dibromohexane, dibromooctane, dibromodecane, dibromododecane, or the like. The compounds are reacted using substantially the same process as described above, with the reaction product being a halogen terminated pendant group-containing compound. The halogen terminated pendant group-containing compound is further reacted with a phenol containing compound, also containing a portion of a pendant group desired to be included, such as 4-hydroxy carboxylic acid or 4-hydroxy biphenyl carboxylic acid. Alternatively, a hydroxyl group-containing benzoic acid sodium salt can be utilized in the reaction. The halogenated pendant group-containing compound is added to a reaction vessel containing a solution of 1,3-dimethyl-3,4,5,6-tetrahydro-2 (1H)-pyrimidinone (DMPU) and phenol group-containing compound (e.g., 4-hydroxy carboxylic acid) with a molar excess of the phenol group-containing compound present compared to the halogen terminated pendant group containing compound. The reaction mixture is stirred at room temperature for a predetermined period of time to complete the reaction, such as about 24 hours, subsequently hydrolyzed with cold, deionized water, and neutralized with an acid such as 1 M hydrochloric acid. The reaction product is extracted with ethyl acetate and dried over sodium sulfate and evaporated to dryness. Recrystallization from ethanol yields a pendant group-containing phenol.

Non-limiting examples of specific pendant groups-containing phenol compounds have been prepared as follows. Reaction schemes are shown to illustrate the described reaction.

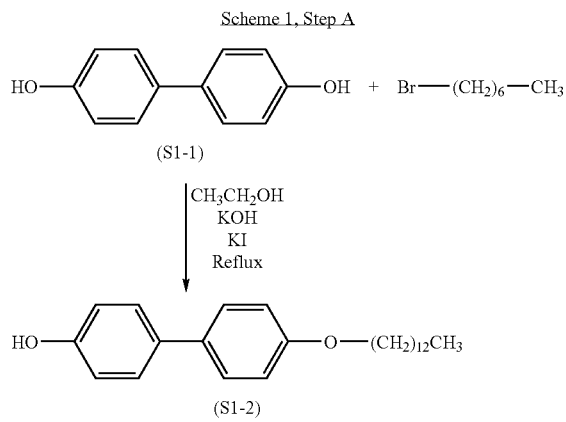

The pendant group-containing phenol (S1-2) of Scheme 1 was prepared as follows:

To a stirred solution of 4,4-biphenol (1 g, 5.12 mmol) and 1-bromohexane (1.75 g, 6.4 mmol) in ethanol, under nitrogen, potassium hydroxide (0.3 g, 5.5 mmol) and a catalytic amount of potassium iodide in ethanol and water (90/10) were added dropwise over 5 hours. After stirring at the reflux temperature under nitrogen for 24 hours, the reaction mixture was concentrated by evaporation of the solvent using a rotary evaporator. The residue was dissolved in ethyl acetate and washed with deionized water. After being dried with sodium sulfate, the solution was evaporated to dryness. Recrystallization from ethanol yielded colorless crystals at a 39% yield (0.72 g, 2.0 mmol). $^1$H NMR (acetone-$d_6$, ppm): $\delta$=7.48 (d, biphenyl, 2H); 7.43 (d, biphenyl, 2H); 6.95 (d, biphenyl, 2H); 6.88 (d, biphenyl, 2H); 4.00 (t, —$CH_2O$—, 2H); 1.77 (q, —$CH_2$—, 2H, 1.48 (q, —$CH_2$—, 2H); 1.37 (q, —$CH_2$—, 2H); 1.20-1.31 (m, $CH_2$, 14H); 0.86 (t, —$CH_3$-3H).

A further example of forming a pendant group-containing phenol is illustrated by the following reaction scheme:

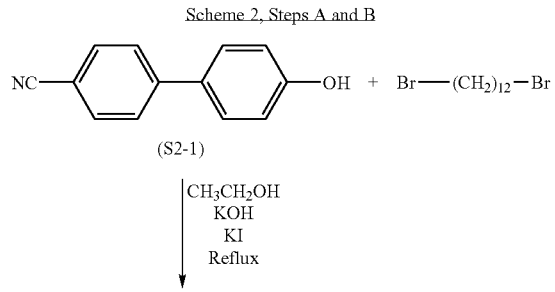

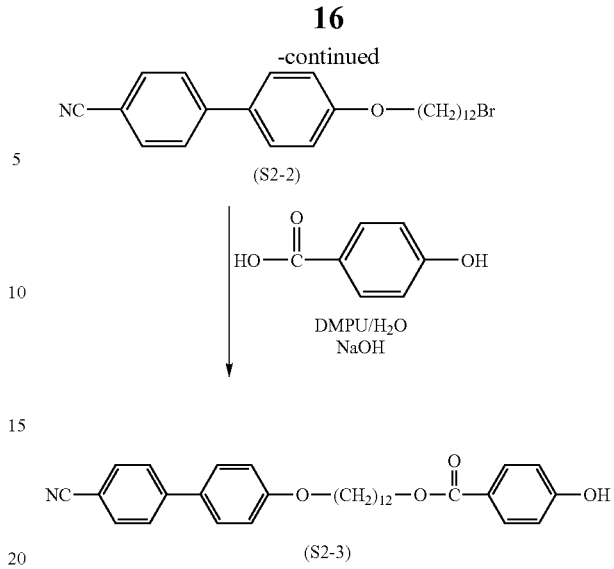

In a first step, compound S2-2 was formed and contained a portion of a pendant group adapted to be added to a phenol for use in forming a benzoxazine monomer was formed as follows: To a stirred solution of 8-nitrile biphenol, compound S2-1 in scheme 2, (1 g, 5.12 mmol), and 1,12-dibromododecane (2.00 g, 6.4 mmol) in ethanol under nitrogen, potassium hydroxide (0.3 g, 5.5 mmol) and a catalytic amount of potassium iodide in ethanol and water (90/10) were added dropwise over 5 hours. After stirring at reflux temperature under nitrogen for 24 hours, the reaction mixture was concentrated by evaporation of the solvent. The residue was dissolved in ethyl acetate and washed with deionized water. After being dried with sodium sulfate, the solution was exposed to dryness. Recrystallization from ethanol yielded colorless 4-[4-12(bromododecyloxy)phenyl]benzeecarbonitrile, S2-2, crystals at an 87% yield (0.65 g, 1.82 mmol). $^1$H NMR (acetone-$d_6$): $\delta$=7.83 (d, phenol, 4H); 7.70 (d, biphenol, 2H, 7.08 (d, biphenyl, 2H); 4.00 (t, —$CH_2O$—, 2H); 3.48 (t, —$CH_2BR$, 2H); 1.77 (m, —$CH_2$—, 2H); 1.18-1.51 (m, —$CH_2$—, 18H).

12-[4(4-cyanophenyl)phenoxyl]dodecyl 4-(4-hydroxy)benzoate, S2-3, was formed from the 4-[4-12(bromododecyloxy)phenyl]benzeecarbonitrile, S2-2, as follows. To a solution of S2-2 (0.5 g, 1.13 mmol) of Scheme 2 in 25 ml of 1,3-dimethyl-3,4,5,6-tetrahydro-2(1H-pyrimidinone (DMPU) was added 4-hydroxycarboxylic acid sodium salt (0.5 g, 3.1 mmol). After stirring at room temperature for 24 hours, the mixture was hydrolyzed with cold, deionized water, neutralized with 1 M HCl, extracted with ethyl acetate, and dried over sodium sulfate. The solution was evaporated to dryness. Recrystallization from ethanol yielded colorless 12-[4(4-cyanophenyl)-phenoxyl]dodecyl 4-(4-hydroxyphenyl)benzoate, S2-3, crystals, at 82% yield (0.40 g, 0.92 mmol). $^1$H NMR (acetone-$d_6$): $\delta$=7.88 (d, phenyl, 2H); 7.83 (d, phenyl, 4H); 7.70 (d, biphenyl, 2H); 7.08 (d, biphenyl, 2H); 6.94 (d, phenyl, 2H); 4.31 (t, —$CH_2COO$—, 2H); 4.00 (t, —$CH_2O$—, 2H); 1.78 (m, —$CH_2$—, 2H); 1.18-1.51 (m, —$CH_2$—, 18H).

A further example of forming a pendant group-containing phenol is illustrated by the following reaction scheme:

Scheme 3, Steps A and B

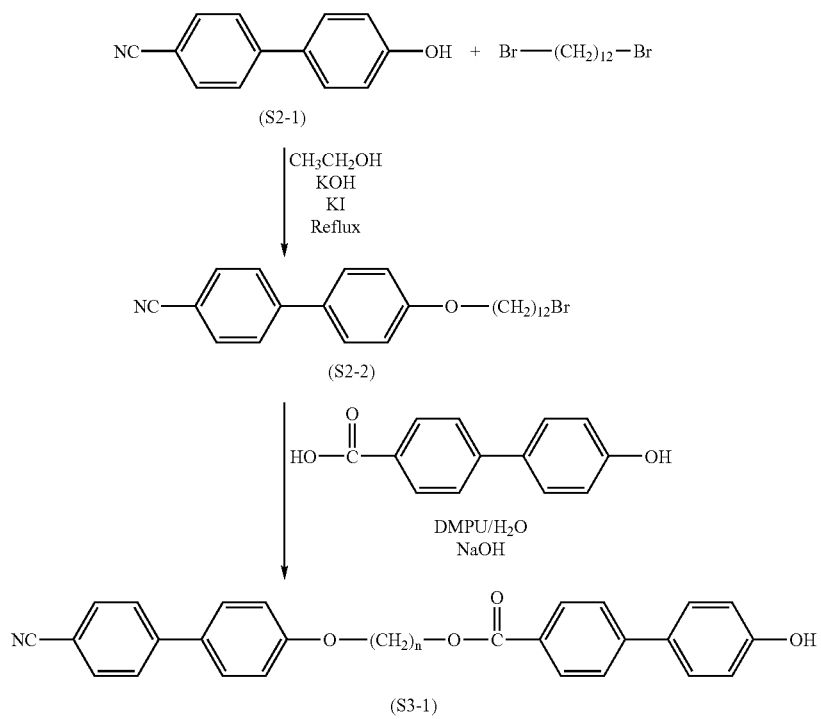

12-[4-[(4-cyanophenyl)phenoxy]dodecyl 4-(4-hydroxyphenyl)benzoate. S3-1 was formed from the 4-[4-12(bromododecyloxy)phenyl]benzeecarbonitrile S2-2 as follows. To a solution of S2-2 (0.5 g, 1.13 mmol) 25 ml of DMPU was added 4-hydroxybiphenylcarboxylic acid (0.5 g, 2.3 mmol). After stirring at room temperature for 24 hours, the mixture was hydrolyzed with cold, deionized water, and neutralized with 1 M HCl. After extracting with ethyl acetate and drying over sodium sulfate, the solution was evaporated to dryness. Recrystallization from ethanol yielded colorless 12-[4-[(4-cyanophenyl)phenoxy]dodecyl 4-(4-hydroxyphenyl)benzoate S3-1 crystals at 73% yield (0.41 g, 0.85 mmol). $^1$H NMR (acetone-$d_6$): δ=8.06 (d, phenyl, 2H); 7.83 (d, phenyl, 4H); 7.73 (d, phenyl, 2H); 7.70 (d, biphenyl, 2H); 7.60 (d, phenyl, 2H); 7.08 (d, biphenyl, 2H); 6.96 (d, phenyl, 2H); 4.31 (t, —CH$_2$COO—, 2H); 4.00 (t, —CH$_2$O—, 2H); 1.78 (m, —CH$_2$—, 2H); 1.18-1.51 (m, —CH$_2$—, 18H).

Benzoxazine monomers are subsequently formed from the aldehyde, amine and phenol components, wherein at least the amine or phenol include at least one pendant group. The pendant group containing benzoxazine monomers can be formed utilizing a solvent or solventless system. A procedure for utilizing solvents to form benzoxazine is described in the literature of benzoxazine monomers. An article by Ning and Ishida in the Journal of Polymer Science, Chemistry Edition, vol. 32, page 1121 (1994) sets forth a procedure using a solvent which can be used to prepare benzoxazine monomers. U.S. Pat. No. 5,543,516, hereby incorporated by reference, sets forth a generally solventless method of forming benzoxazine monomers.

Multi-functional benzoxazines of the invention are prepared by the condensation of a multi-functional phenol, formaldehyde, and a primary amine, with the amine or phenol comprising at least one pendant group according to the invention.

The phenols of the present invention optionally contain one or more pendant groups in an ortho, meta and/or para position. Suitable non-limiting examples of phenols may also be substituted with one or more aliphatics, straight chain or branched aliphatics, aromatic groups, halogen groups, hydrogen or amine, in which at least one of the ortho positions of the phenol ring is unsubstituted. Other suitable substitutes known to the art can also be utilized.

Monofunctional phenols include, but are limited to, phenol, cresol, 2-bromo-4-methylphenol, 2-allylphenol and 1,4-aminophenol. Suitable di-functional phenols include, but are not limited to, phenolphthalane, biphenol, 4-4'-methylene-diphenol, 4-4'-dihydroxybenzophenone, bisphenol-A, 1,8-dihydroxy-anthraquinone, 1,6-dihydroxy-naphthalene, 2,2'-dihydroxyazobenzene, resorcinol, and fluorine bisphenol. Tri-functional phenols include, but are limited to, 1,3,5-trihydroxy benzene.

The aldehydes and aldehyde derivatives used to form the benzoxazine monomers can be any aldehyde such as formaldehyde, or aldehyde derivatives such as, but not limited to, paraformaldehyde and polyoxymethylene, with formaldehyde and paraformaldehyde being preferred. The aldehydes have the general formula RCHO, where R is hydrogen; an aliphatic having 1 to about 6 carbon atoms; or a cyclic group having from about 1 to about 12 carbon atoms, with 1 to about 6 carbon atoms being preferred. Preferably R is hydrogen. Mixtures of aldehydes and/or aldehyde derivatives can be utilized.

The amines optionally contain a pendant group and can be mono-functional or poly-functional. Primary amines are required in order to obtain a benzoxazine ring structure. The primary amines may have aliphatic substituents, aromatic substituents, or combinations thereof, and also may include heteroatoms. Additional suitable amine reactants are known in the art. The amine may include secondary amine groups or any other functional group in addition to the required primary amine.

Examples of monofunctional amines include, but are not limited to, ammonium, methylamine, ethylamine, propylamine, butylamine, isopropylamine, octadecylamine, cyclohexylamine, alkylamine, 1-aminoanthracene, 4-aminobenzaldehyde, 4-aminobenzophenone, aminobiphenyl, 2-amino-5-bromophridine, D-3-amino-e-caprolactam, 2-amino-2,6-dimethylpiperidine, 3-amino-9-ethylcarbazole, 4-(2-aminoethyl)morpholine, 2-aminofluorenone, 2-aminofluorene, 1-aminohomopiperidine, 9-aminophenanthrene, 1-aminopyrene, 4-bromoaniline and aniline.

Suitable di-functional amines include, but are not limited to, 2-aminobenxylamine, 1,3-diaminopropane, 1,4-diaminobutane, 1,10-diaminodecane, 2,7-diaminofluorene, 1,4-diaminocyclohexane, 9,10-diaminophenanthrene, 1,4-diaminopiperazine, 1,4-methylenedianiline, 1,4-diaminobenzophenone, 4,4-diamonodiphenyl-sulfone, methylenedianiline, fluorenediamine, 4,4'-diaminodiphenyl-sulfide, and 4,4-oxydianile.

Suitable tri-functional amines include, but are not limited to, melamine, etc., while tetra-functional amines comprise fluorenetetraamine and tetraminediphenylether.

The reaction time for forming the monofunctional benzoxazine monomers can vary widely and depend on reactant concentration, reactivity of the reactants, and temperature. Reaction time can vary from a few minutes for a solventless reaction, or from about a few minutes to about 100 hours and preferably from about 1 to about 50 hours when utilizing solvents. Solid components may be premixed as solids and subsequently melted; or first melted and then mixed. The temperature of reaction is determined by routine experimentation as known to those of ordinary skill in the art, noting the formation of benzoxazine and less desired products and optimizing temperature and time for a desirable product. Reaction temperatures generally range from about 0° C. to about 160° C., desirably from about room temperature to about 155° C., and preferably from about 50° C. to about 150° C.

The synthesis of monobenzoxazine monomers comprising at least one pendant group may be conducted at atmospheric pressure or at pressures up to about 100 psi. In some instances, a reaction carried out under pressure may be preferred in order to produce fewer by-products. The relative amounts of reactants required will depend upon their chemical nature, e.g., the number of reactive groups taking part in the reaction. The stoichiometry is well within the skills of those conversant with the art and the relative required amounts of reactants are readily selected depending on the functionality of the reacting compounds. The reacted mixture contains the desired benzoxazine monomer containing at least one pendant group, and possibly impurities. If desired, the mixture may be purified to obtain a more concentrated form of the product, for example by well known crystallization or solvent washing techniques.

The following examples are meant to illustrate, but not to limit, the formation of benzoxazine monomers comprising at least one pendant group.

In a first embodiment, pendant group-containing benzoxazine monomers are formed from the pendant group containing phenol 4-dodecyloxy-1-(3 methyl(2H, 4H-benzo[3,4-e]1,3-oxazaperhydroin-6-yl)benzene, S1-2, prepared hereinabove as shown in the following reaction scheme.

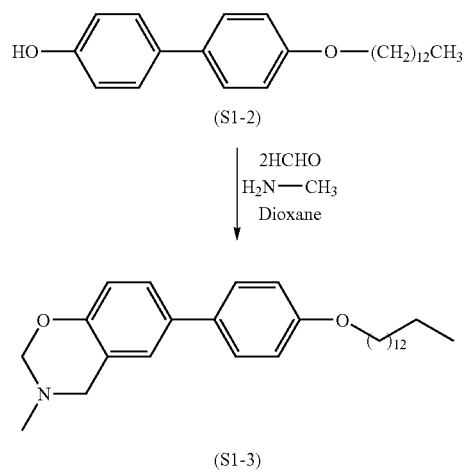

The pendant group-containing phenol 4-dodecyloxy-1-(3 methyl(2H, 4H-benzo[3,4-e]1,3-oxazaperhydroin-6-yl)benzene, methylamine, and formaldehyde in a 1:1:2 mole ratio were added to a flask in which dioxane was present as solvent.

Solute concentration was set to 10 weight % and the composition was stirred at 90° C. for 300 minutes to complete the reaction. Then solvent was evaporated.

The benzoxazine monomer reaction product S1-3 shown above was then dissolved in dichloromethane, filtered and washed with alkaline water. The solvent was evaporated using a rotary evaporator and the benzoxazine monomer, including a pendant group containing a benzene ring having an alkoxy group connected thereto, was vacuum dried. $^1$H NMR (acetone-d$_6$, ppm): δ=7.85 (s, biphenyl, 2H); 7.50 (d, biphenyl, 2H); 7.20 (d, biphenyl, 2H); 4.75 (s, —O—CH$_2$—N<, 2H); 3.90 (s, >N—CH$_2$-phenyl, 2H); 4.00 (t, —CH$_2$O—, 2H); 1.77 (mult, —CH$_2$CH$_2$O—, 2H); 1.18-1.51 (m, —CH$_2$—, 6H). The $^1$H NMR signals were in agreement with the expected chemical structure.

In a further embodiment, a pendant group-containing benzoxazine monomers were formed utilizing the pendant group-containing phenol, 12[4-(4-cyanophenyl)phenoxy] dodecyl 4-(4-hydroxyphenyl)benzoate), compound S2-3, shown above. The reaction scheme is shown below.

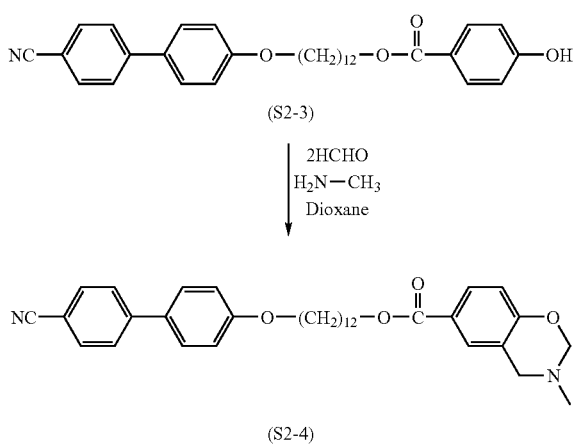

The pendant group-containing phenol 12[4-(4-cyanophenyl)phenoxy]dodecyl 4-(4-hydroxyphenyl)benzoate) (compound S2-3), methylamine, and formaldehyde in a 1:1:2 mole ratio were added to a flask in which dioxane is present as solvent. Solute concentration was set to 10 weight % and stirred at 90° C. for 300 minutes to complete the reaction. The solvent was evaporated.

The pendant group-containing benzoxazine monomer reaction product S2-4 shown above was then dissolved in dichloromethane, filtered and washed with alkaline water. The solvent was evaporated using a rotary evaporator and the product was vacuum dried. As illustrated, the benzoxazine monomer S2-4 includes a pendant group comprising a carbonyl group, alkoxy group, 2 benzene rings and a nitrile group. $^1$H NMR (acetone-$d_6$): $^1$H NMR (acetone-$d_6$): δ=7.83 (d, phenyl, 4H); 7.77 (d, phenyl, 1H); 7.69 (s, phenyl, 1H); 7.70 (d, biphenyl, 2H); 7.08 (d, biphenyl, 2H); 6.79 (d, phenyl, 1H); 4.86 (s, —O—$CH_2$—N<, 2H); 4.31 (t, —$CH_2$COO—, 2H); 4.00 (t, —$CH_2$O—, 2H); 3.95 (s, >N—$CH_2$-phenyl, 2H); 1.78 (m, —$CH_2$—, 2H); 1.18-1.51 (m, —$CH_2$—, 18H). FTIR (KBr, cm$^{-1}$) 2948 (aliphatic $CH_2$,) 2850 (aliphatic $CH_2$), 2225 (CN), 1605 (C=O), 1500 (tri-sub benzene ring), 938 (tri-sub benzene ring). The $^1$H NMR signals were in agreement with the expected chemical structure.

In a further embodiment, pendant group-containing benzoxazine monomers were formed utilizing the pendant group containing phenol S3-1 shown above. The reaction scheme is shown below.

concentration was set to 10 weight % and stirred at 90° C. for 300 minutes. Then solvent was evaporated.

The pendant group-containing benzoxazine monomer reaction product S3-2 shown above was then dissolved in dichloromethane, filtered and washed with alkaline water. The solvent was evaporated using a rotary evaporator and the product was vacuum dried. As illustrated, the benzoxazine monomer S3-2 includes a pendant group comprising a carbonyl group, alkoxy group, 2 benzene rings and a nitrile group. $^1$H NMR (acetone-$d_6$): δ=8.06 (d, phenyl, 2H); 7.83 (d, phenyl, 4H); 7.73 (d, phenyl, 2H); 7.70 (d, biphenyl, 2H); 7.59 (d, phenyl, 1H); 7.40 (s, phenyl, 1H); 7.08 (d, biphenyl, 2H); 6.83 (d, phenyl, 2H); 4.81 (s, —O—$CH_2$—N<, 2H); 4.31 (t, —$CH_2$COO—, 2H); 4.00 (t, —$CH_2$O—, 2H); 3.98 (s, >N—$CH_2$-phenyl, 2H) 1.78 (m, —$CH_2$—, 2H); 1.18-1.51 (m, —$CH_2$—, 18H). FTIR (KBr, cm$^{-1}$) 2948 (aliphatic $CH_2$,) 2850 (aliphatic $CH_2$), 2225 (CN), 1605 (C=O), 1500 (tri-sub benzene ring), 938 (tri-sub benzene ring). The $^1$H NMR signals were in agreement with the expected chemical structure.

Pendant Group-Containing Benzoxazine (Co)Polymers

Pendant group-containing (co)polymers (i.e., polymer or copolymers) are formed from the benzoxazine monomers containing at least one pendant group. Either benzoxazine polymers or copolymers can be formed. Copolymers can be derived from two or more pendant group-containing monomers having different structures or at least one pendant group-containing benzoxazine monomer and one or more monomers which do not contain a pendant group. In a preferred embodiment the pendant group-containing (co)polymers have the pendant groups located in the side chain(s) thereof.

The benzoxazine monomers comprising a pendant group are capable of undergoing ring-opening polymerization in a variety of ways, including thermal initiation in the absence of

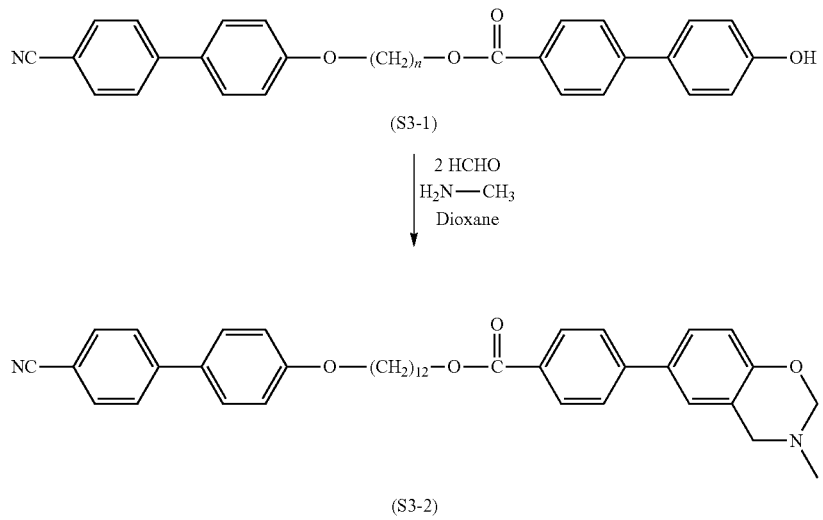

Scheme 3, Step C

The pendant group-containing phenol 12[4-[(4-cyanophenyl)phenoxy]dodecyl 4-(4-hydroxyphenyl)benzoate) S3-1, methylamine, and formaldehyde in a 1:1:2 mole ratio were added to a flask in which dioxane is present as solvent. Solute a catalyst or cationic initiation in the presence of a catalyst. Cationic polymerization of benzoxazine monomers is described in U.S. Pat. No. 6,225,440 to Ishida, herein incorporated by reference.

The pendant group-containing benzoxazine monomers unexpectedly polymerize at temperatures which are generally lower than benzoxazine monomers not containing pendant groups. Polymerization at temperatures as low as 100° C. have been observed.

The following reaction schemes illustrate the pendant group-containing benzoxazine polymers formed from the pendant group-containing benzoxazine monomers described hereinabove.

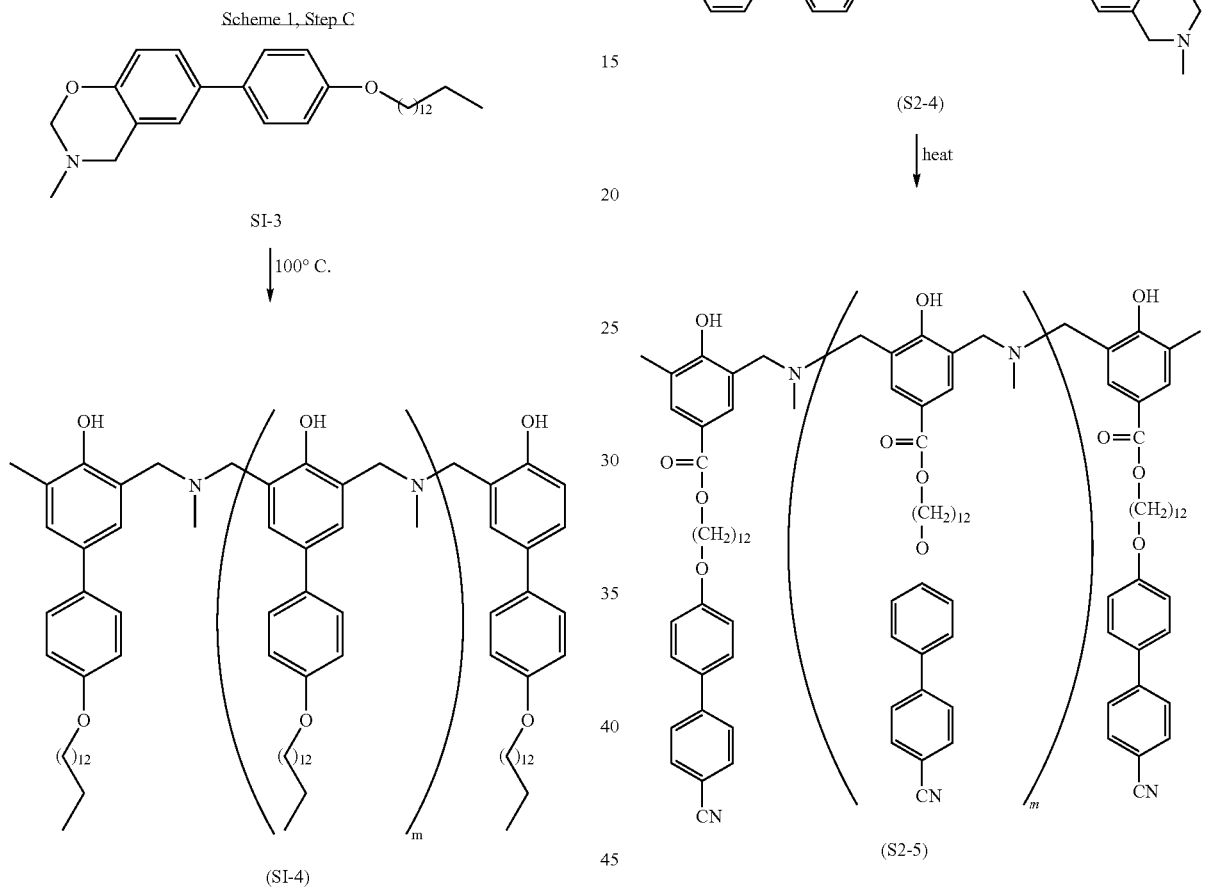

(SI-4)

wherein m is believed to be about 2 to about 30.

The pendant group-containing polymer (S1-4) shown above was polymerized isothermally from the pendant group-containing benzoxazine monomers (S1-3) at a temperature of about 175° C. for about 120 minutes in a DSC hermetic pan with a flow rate of 60 ml/min of nitrogen. No catalyst was needed to perform the polymerization. The polymerization procedure was also performed utilizing benzoxazine monomers similar to S1-3, but having 6 and 8 methylene unit spacer groups.

Scheme 2, Step 2 illustrates pendant group-containing benzoxazine polymers, S2-5, formed from pendant group-containing benzoxazine monomers.

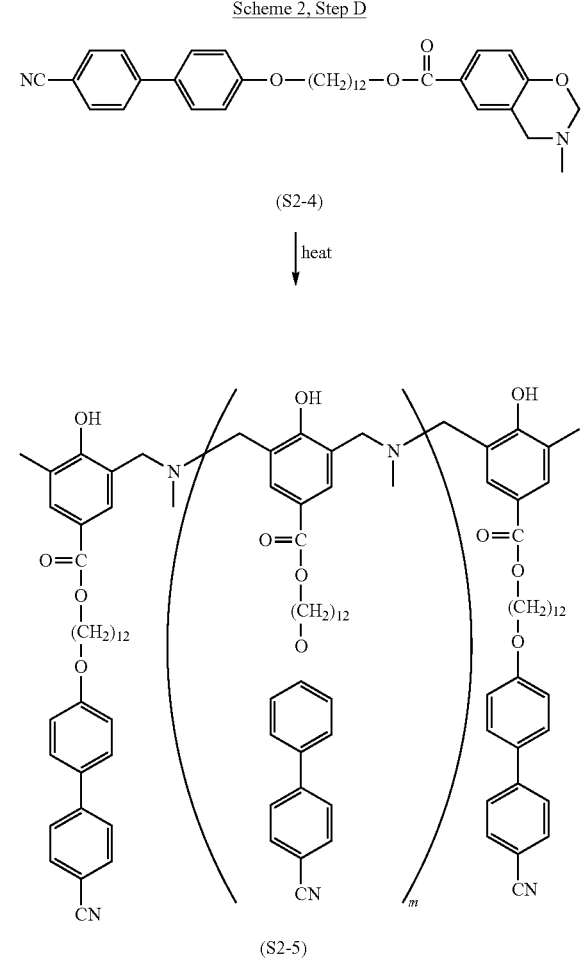

wherein m is believed to be about 2 to about 30.

The pendant group-containing polymer S2-5 shown above was prepared by heating the pendant group-containing benzoxazine monomers S2-4 at a temperature of about 175° C. for about 120 minutes in a DSC hermetic pan with a flow rate of 60 ml/min of nitrogen. No catalyst was needed to perform the polymerization. The polymerization procedure was also performed utilizing benzoxazine monomers having 6 and 8 methylene unit spacer groups.

Scheme 3

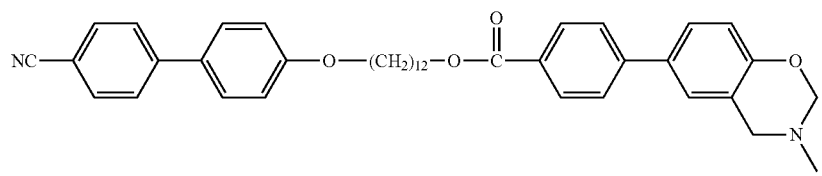

(S3-2)

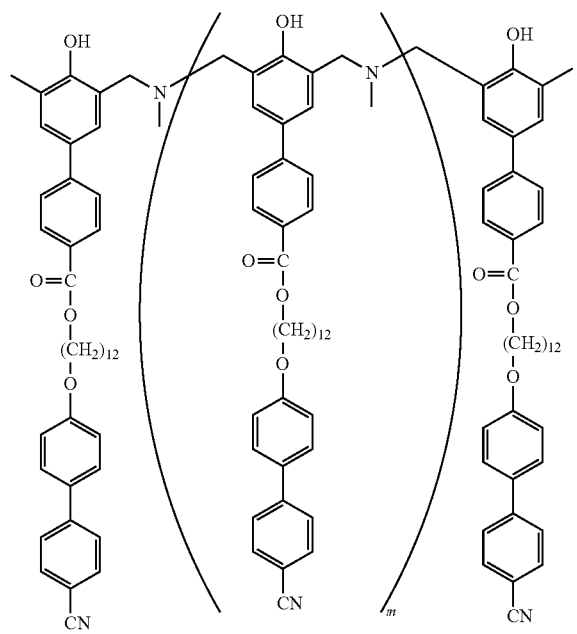

wherein m is believed to be about 2 to about 30.

The pendant group-containing polymer S3-3 shown above was prepared by heating the pendant group-containing benzoxazine monomers S3-2 at a temperature of about 175° C. for about 120 minutes in a DSC hermetic pan with a flow rate of 60 ml/min of nitrogen. No catalyst was needed to perform the polymerization. The polymerization procedure was also performed utilizing benzoxazine monomers having 6 and 8 methylene unit spacer groups.

As illustrated in FIG. 1, pendant group-containing benzoxazine monomer (S2-4) having a spacer group of 12 methylene repeat units exhibited a polymerization exotherm at 170° C., whereas the 6 and 8 methylene unit spacer groups were slightly higher. The DSC thermogram shows that the polymerization temperature is believed to be dependent on the length of chain and, therefore, on the order in the molecule. The pendant group-containing benzoxazine polymer S2-4 having a 12 methylene unit spacer group exhibits nematic order, whereas the benzoxazine polymers having 6 and 8 methylene unit spacer groups show smectic and substantially non-liquid crystalline transitions, respectively.

FT-IR were utilized to confirm the benzoxazine ring opening reaction.

As illustrated in FIG. 2, the pendant group-containing benzoxazine monomer S2-4 having a 12 methylene unit spacer group exhibits low temperature polymerization. After heating at 1000 for 2 hours, absorbance peaks at 923 and 934 cm$^{-1}$ are completely missing. Those peaks are characteristic modes of benzene with an attached oxazine ring, so it shows the polymerization is completed after heating.

The pendant group-containing benzoxazine monomers and polymers described in the present invention have many uses including, but not limited to, optical materials, electronic materials such as fiber reinforced boards for electronics, chip coatings or overlay materials, adhesives or resins for electronic applications, fireproofing materials, and the like.

While in accordance with the patent statutes the best mode and preferred embodiment have been set forth, the scope of the invention is not limited thereto, but rather by the scope of the attached claims.

What is claimed is:

1. A benzoxazine group-containing monomer having a pendant group, comprising:

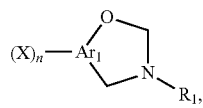

Formula 1

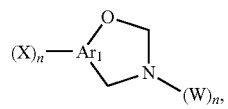

Formula 2

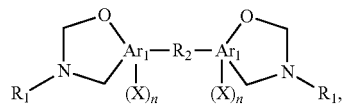

Formula 3

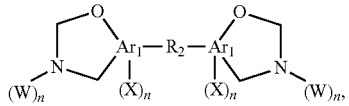

Formula 4

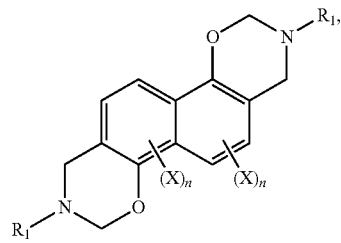

Formula 5

-continued

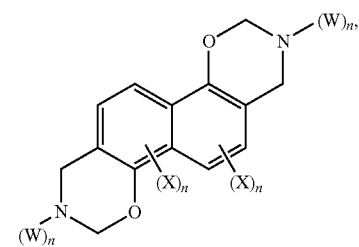

Formula 6

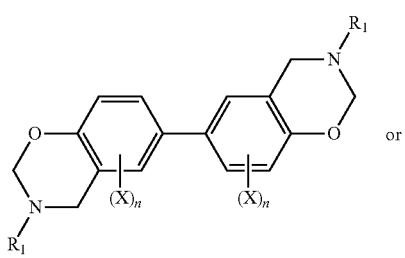

Formula 7

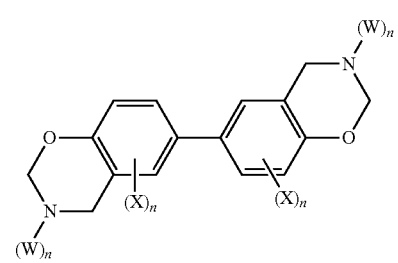

Formula 8 wherein each n, independently, is an integer from 0 to 2, with the proviso that at least one n of each formula is 1 or 2;

wherein each $Ar_1$, independently is one or more optionally substituted aromatic rings having from 6 to 18 carbon atoms, wherein each $R_1$, independently, is a linear or branched, optionally substituted, alkyl group, for example having from 1 to about 18 carbon atoms, a mono- or polyfluorinated alkyl having from 1 to about 9 carbon atoms, an aromatic having from 6 to about 18 carbon atoms, or an alkyl substituted aromatic or aromatic substituted alkyl of 7 to about 40 carbon atoms;

wherein $R_2$ comprises:

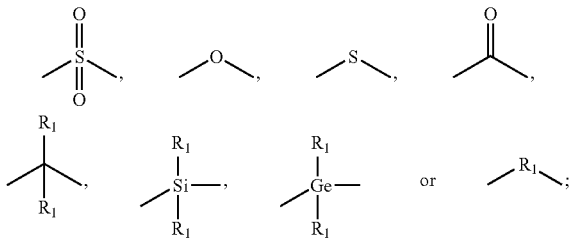

wherein X is —Z—Y-Sp-Z—Y-Sp-Z—Y-Sp; wherein one or more Z, Y, or Sp are optionally absent, with the proviso that at least one Z is present and when one or more Z, Y or Sp are absent, the present adjacent components are directly connected, with the proviso that when $Ar_1$ is benzene and Z is a hydrocarbon aromatic containing one or more aromatic rings, at least one or more Y and Sp are present and include one or more heteroatoms;

wherein each Z, independently, is selected from one of the following rings:

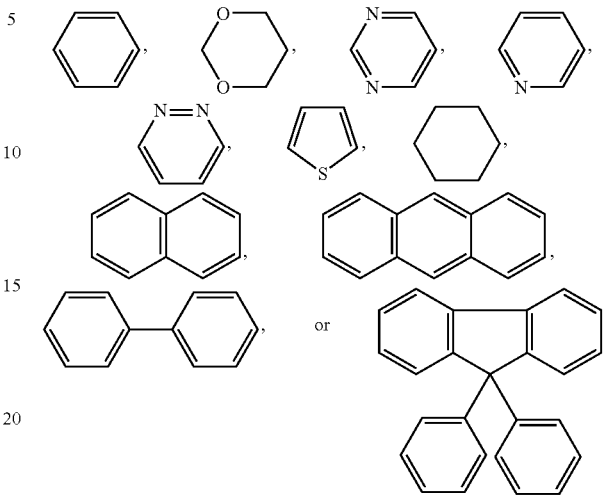

wherein any of the Z rings, independently, is optionally substituted with one or more of the following substituents in at least one of the available substitution positions: F, Cl, Br, $CH_3$, CN, OR, R and NCS where R is a branched or straight chain alkyl having from 1 to about 5 carbon atoms;

wherein each Y, independently, is selected from COO, OCO, $CH_2$, $CHCH_2CH_2$, $CH_2O$, $OCH_2$, —$C(CH_3)_2$—, O, S, N, CH=N, $C(CH_3)$=N, $C(CH_3)$=CH, $C(CH_3)$=$C(CH_3)$, CH=CH or C≡C;

wherein each spacer group Sp, independently, is optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, an alkoxy having from 1 to about 20 carbon atoms, an alkoxycarbonyl having from 1 to about 20 carbon atoms, an alkylcarbonyl having from 1 to about 20 carbon atoms, or an alkylcarbonyloxy having from 1 to about 20 carbon atoms, or a corresponding intermediate chain group;

wherein each W, independently, is —Z—Y-$Sp_w$-Z—Y-$Sp_w$-Z—Y-$Sp_w$; wherein one or more Z, Y, or $Sp_w$ are optionally absent with the proviso that at least one Z is present, and when one or more Z, Y, or $Sp_w$ are absent, the present adjacent components are directly connected; and wherein each $Sp_w$, independently, is optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, alkoxy having from 5 to about 20 carbon atoms, alkoxycarbonyl having from 1 to about 20 carbon atoms, alkylcarbonyl having from 1 to about 20 carbon atoms, or alkylcarbonyloxy having from 1 to about 20 carbon atoms, or a corresponding intermediate chain group.

2. The benzoxazine group-containing monomer according to claim 1, wherein the n of at least one $X_n$ is 1 or 2.

3. The benzoxazine group-containing monomer according to claim 2, wherein X includes at least one Z and at least one Sp.

4. The benzoxazine group-containing monomer according to claim 3, wherein the at least one Sp is the alkoxy having from 1 to about 20 carbon atoms, the alkoxycarbonyl having from 1 to about 20 carbon atoms, the alkylcarbonyl having from 1 to about 20 carbon atoms, or the alkylcarbonyloxy having from 1 to about 20 carbon atoms, or the corresponding intermediate chain group.

5. The benzoxazine group-containing monomer according to claim 1, wherein at least one X is

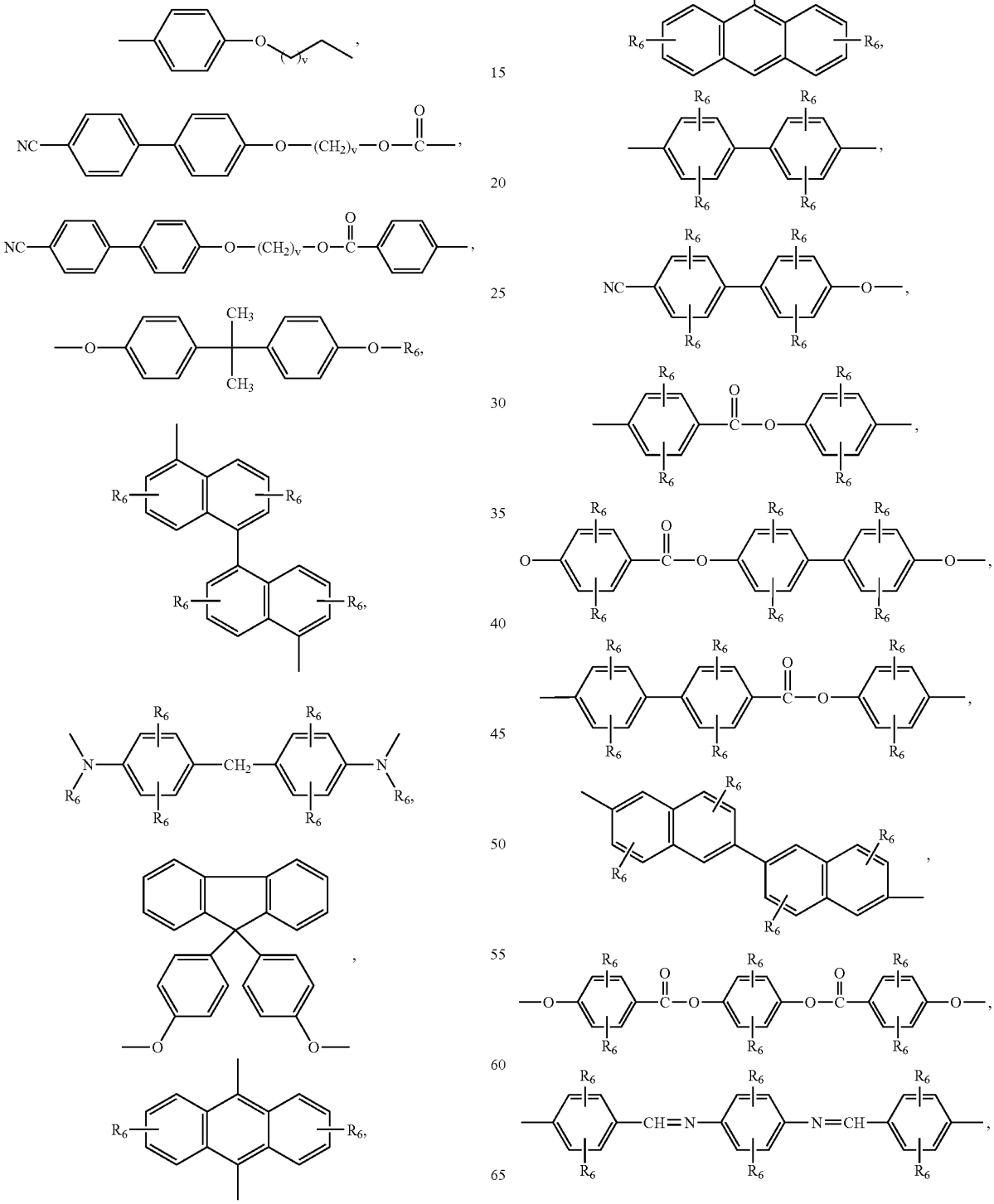

-continued

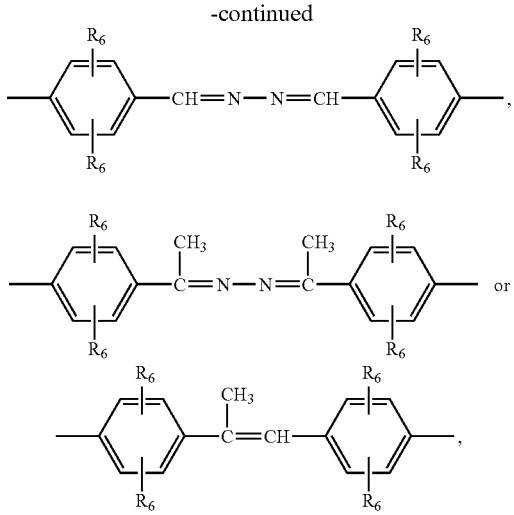

wherein each $R_6$, independently, is hydrogen, an aliphatic group having from 1 to about 12 carbon atoms, or a halogen atom, and wherein v is 1 to about 20 carbon atoms.

6. The benzoxazine group-containing monomer according to claim 1, wherein the monomer has the formula:

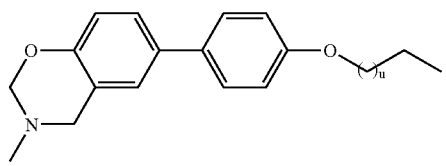

wherein u is 1 to about 20.

7. The benzoxazine group-containing monomer according to claim 1, wherein the monomer has the formula:

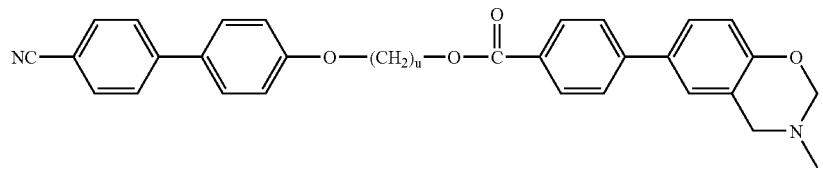

wherein u is 1 to about 20.

8. The benzoxazine group-containing monomer according to claim 1, wherein the monomer has the formula:

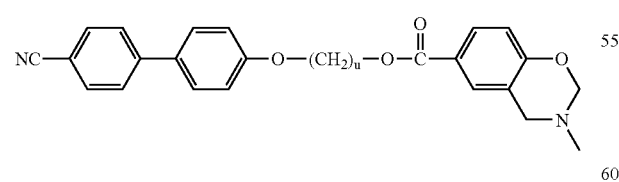

wherein u is 1 to about 20.

9. The benzoxazine group-containing monomer according to claim 1, wherein X includes at least one Z and at least Sp.

10. The benzoxazine group-containing monomer according to claim 1, wherein at least one Sp is present and is the alkoxy having from 1 to about 20 carbon atoms, the alkoxycarbonyl having from 1 to about 20 carbon atoms, the alkyl- carbonyl having from 1 to about 20 carbon atoms, or the alkylcarbonyloxy having from 1 to about 20 carbon atoms, or a corresponding intermediate chain group.

11. The benzoxazine group-containing monomer according to claim 10, wherein the alkoxy has from 8 to about 20 carbon atoms, the alkoxycarbonyl has from 8 to about 20 carbon atoms, the alkylcarbonyl has from 8 to about 20 carbon atoms, or the alkylcarbonyloxy has from 8 to about 20 carbon atoms, or a corresponding intermediate chain group.

12. The benzoxazine group-containing monomer according to claim 10, wherein the alkoxy has from 10 to about 20 carbon atoms, the alkoxycarbonyl has from 10 to about 20 carbon atoms, the alkylcarbonyl has from 10 to about 20 carbon atoms, or the alkylcarbonyloxy has from 10 to about 20 carbon atoms, or a corresponding intermediate chain group.

13. A polymer or copolymer including at least one repeat unit derived from at least one benzoxazine group-containing monomer according to claim 1.

14. A polymer or copolymer including at least one repeat unit derived from at least one benzoxazine group-containing monomer according to claim 4.

15. The polymer or copolymer including at least one repeat unit derived from at least one benzoxazine group-containing monomer according to claim 5.

16. An optical material, electronic material, adhesive or resin derived from at least one monomer according to claim 1.

17. An optical material, electronic material, adhesive or resin derived from at least one monomer according to claim 3.

18. An optical material, electronic material, adhesive or resin derived from at least one monomer according to claim 5.

19. A method for forming a benzoxazine group-containing monomer, comprising the steps of:
providing a phenol compound, an aldehyde, and a primary amine, wherein at least the primary amine or phenol compound includes at least one pendant group; and
forming a pendant group-containing benzoxazine monomer having the following formula:

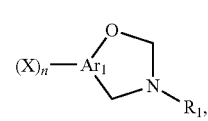

Formula 1

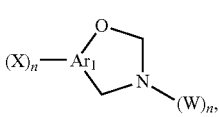

Formula 2

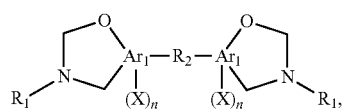

Formula 3

Formula 4
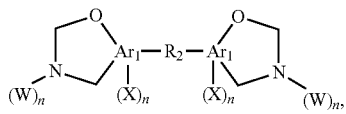

Formula 5
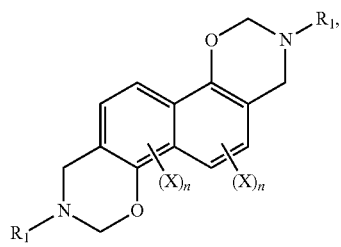

Formula 6
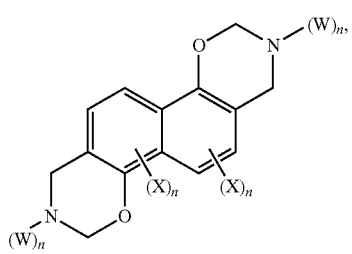

Formula 7
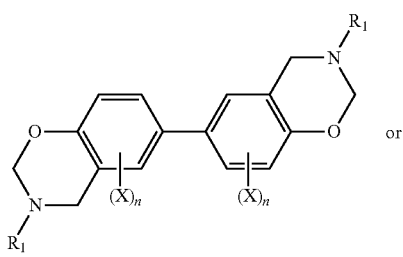

or

Formula 8
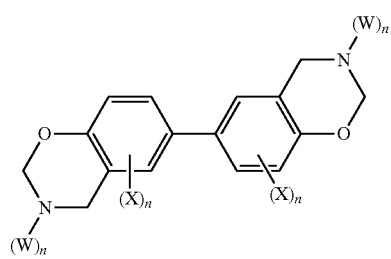

wherein each n, independently, is an integer from 0 to 2, with the proviso that at least one n of each formula is 1 or 2;

wherein each $Ar_1$, independently is one or more optionally substituted aromatic rings having from 6 to 18 carbon atoms, wherein each $R_1$, independently, is a linear or branched, optionally substituted, alkyl group, for example having from 1 to about 18 carbon atoms, a mono- or polyfluorinated alkyl having from 1 to about 9 carbon atoms, an aromatic having from 6 to about 18 carbon atoms, or an alkyl substituted aromatic or aromatic substituted alkyl of 7 to about 40 carbon atoms;

wherein $R_2$ comprises:

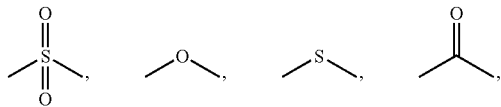

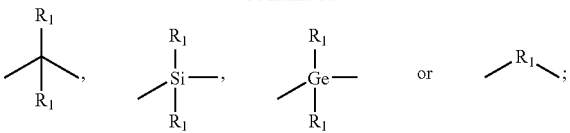

wherein X is —Z—Y-Sp-Z—Y-Sp-Z—Y-Sp; wherein one or more Z, Y, or Sp are optionally absent, with the proviso that at least one Z is present and when one or more Z, Y or Sp are absent, the present adjacent components are directly connected, with the proviso that when $Ar_1$ is benzene and Z is a hydrocarbon aromatic containing one or more aromatic rings, at least one or more Y and Sp are present and include one or more heteroatoms;

wherein each Z, independently, is selected from one of the following rings:

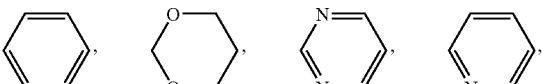

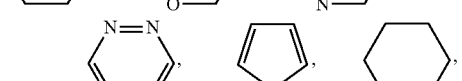

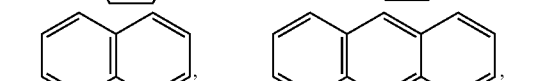

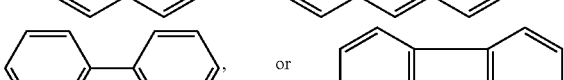

wherein any of the Z rings, independently, is optionally substituted with one or more of the following substituents in at least one of the available substitution positions: F, Cl, Br, $CH_3$, CN, OR, R and NCS where R is a branched or straight chain alkyl having from 1 to about 5 carbon atoms;

wherein each Y, independently, is selected from COO, OCO, $CH_2$, $CHCH_2CH_2$, $CH_2O$, $OCH_2$, —$C(CH_3)_2$—, O, S, N, CH=N, $C(CH_3)$=N, $C(CH_3)$=CH, $C(CH_3)$=$C(CH_3)$, CH=CH or C≡C;

wherein each spacer group Sp, independently, is optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, an alkoxy having from 1 to about 20 carbon atoms, an alkoxycarbonyl having from 1 to about 20 carbon atoms, an alkylcarbonyl having from 1 to about 20 carbon atoms, or an alkylcarbonyloxy having from 1 to about 20 carbon atoms, or a corresponding intermediate chain group;

wherein each W, independently, is —Z—Y-$Sp_w$-Z—Y-$Sp_w$-Z—Y-$Sp_w$; wherein one or more Z, Y, or $Sp_w$ are optionally absent with the proviso that at least one Z is present, and when one or more Z, Y, or $Sp_w$ are absent, the present adjacent components are directly connected; and wherein each $Sp_w$, independently, is optionally substituted, saturated or unsaturated, straight chain or branched chain alkyl or alkylene group having from 1 to about 80 carbon atoms, with one or more of the non-adjacent alkyl $CH_2$ groups being optionally replaced by one or more heteroatoms, alkoxy having from 5 to about 20 carbon atoms, alkoxycarbonyl having from 1 to about 20 carbon atoms, alkylcarbonyl having from 1 to about 20 carbon atoms, or alkylcarbonyloxy having from 1 to about 20 carbon atoms, or a corresponding intermediate chain group.

20. The method according to claim 19, wherein at least one Sp is present and is the alkoxy having from 1 to about 20 carbon atoms, the alkoxycarbonyl having from 1 to about 20 carbon atoms, the alkylcarbonyl having from 1 to about 20 carbon atoms, or the alkylcarbonyloxy having from 1 to about 20 carbon atoms, or a corresponding intermediate chain group.

\* \* \* \* \*